United States Patent
Thevenet

(10) Patent No.: US 6,962,594 B1
(45) Date of Patent: Nov. 8, 2005

(54) REINFORCEMENT IMPLANTS FOR TISSUE SUTURES

(76) Inventor: Fabrice Thevenet, 24, allée de Verdun, 69500 Bron (FR)

( * ) Notice: Subject to any disclaimer, the term of this patent is extended or adjusted under 35 U.S.C. 154(b) by 0 days.

(21) Appl. No.: 09/674,275

(22) PCT Filed: Apr. 20, 1999

(86) PCT No.: PCT/FR99/00934

§ 371 (c)(1),
(2), (4) Date: Oct. 30, 2000

(87) PCT Pub. No.: WO99/55397

PCT Pub. Date: Nov. 4, 1999

(30) Foreign Application Priority Data

Apr. 29, 1998 (FR) .............................................. 98 05688

(51) Int. Cl.[7] .............................................. A61B 17/08
(52) U.S. Cl. .................................... 606/151; 227/175.1
(58) Field of Search ................................ 606/232, 233, 606/151; 604/367, 374, 375; 227/175.1

(56) References Cited

U.S. PATENT DOCUMENTS

| | | | | |
|---|---|---|---|---|
| 3,108,357 A | * | 10/1963 | Lieberg | 138/123 |
| 3,155,095 A | * | 11/1964 | Brown | 285/260 |
| 3,525,340 A | * | 8/1970 | Gilbert | 602/46 |
| 3,779,247 A | * | 12/1973 | Nolan et al. | 24/100.5 |
| 3,951,155 A | * | 4/1976 | Prouse et al. | 131/352 |
| 4,452,245 A | * | 6/1984 | Usher | 606/151 |
| 4,534,349 A | * | 8/1985 | Barrows | 606/152 |
| 4,773,902 A | | 9/1988 | Lentz et al. | |
| 4,840,626 A | | 6/1989 | Linsky et al. | |
| 4,877,037 A | * | 10/1989 | Ko et al. | 600/569 |
| 5,002,551 A | | 3/1991 | Linsky et al. | |
| 5,061,283 A | * | 10/1991 | Silvestrini | 128/898 |
| 5,565,094 A | * | 10/1996 | Zoch et al. | 184/6.11 |
| 5,684,051 A | * | 11/1997 | Thompson | 514/777 |
| 5,718,862 A | * | 2/1998 | Thompson | 264/294 |
| 5,753,110 A | * | 5/1998 | Matsumura et al. | 210/150 |
| 5,756,632 A | * | 5/1998 | Ward et al. | 210/500.21 |
| 5,820,918 A | * | 10/1998 | Ronan et al. | 424/423 |
| 5,879,359 A | * | 3/1999 | Dorigatti et al. | 606/152 |
| 6,114,594 A | * | 9/2000 | Barikosky | 602/43 |
| 6,174,323 B1 | * | 1/2001 | Biggs et al. | 606/144 |
| 2001/0031978 A1 | * | 10/2001 | Kipke et al. | 606/191 |

FOREIGN PATENT DOCUMENTS

| | | | | |
|---|---|---|---|---|
| WO | WO 8702877 | * | 5/1987 | A61B/10/00 |
| WO | WO 96/02285 | | 2/1996 | |

* cited by examiner

*Primary Examiner*—Michael J. Milano
*Assistant Examiner*—D. Jacob Davis
(74) *Attorney, Agent, or Firm*—Stites & Harbison PLLC; Ross F. Hunt, Jr.

(57) ABSTRACT

The invention concerns a reinforcing implant for tissue sutures used for mechanically reinforcing stitched tissue zones, and consisting of a textile lap based on polyuronic acid or one of its salts

16 Claims, 2 Drawing Sheets

REINFORCEMENT IMPLANTS FOR TISSUE SUTURES

Figure 1:
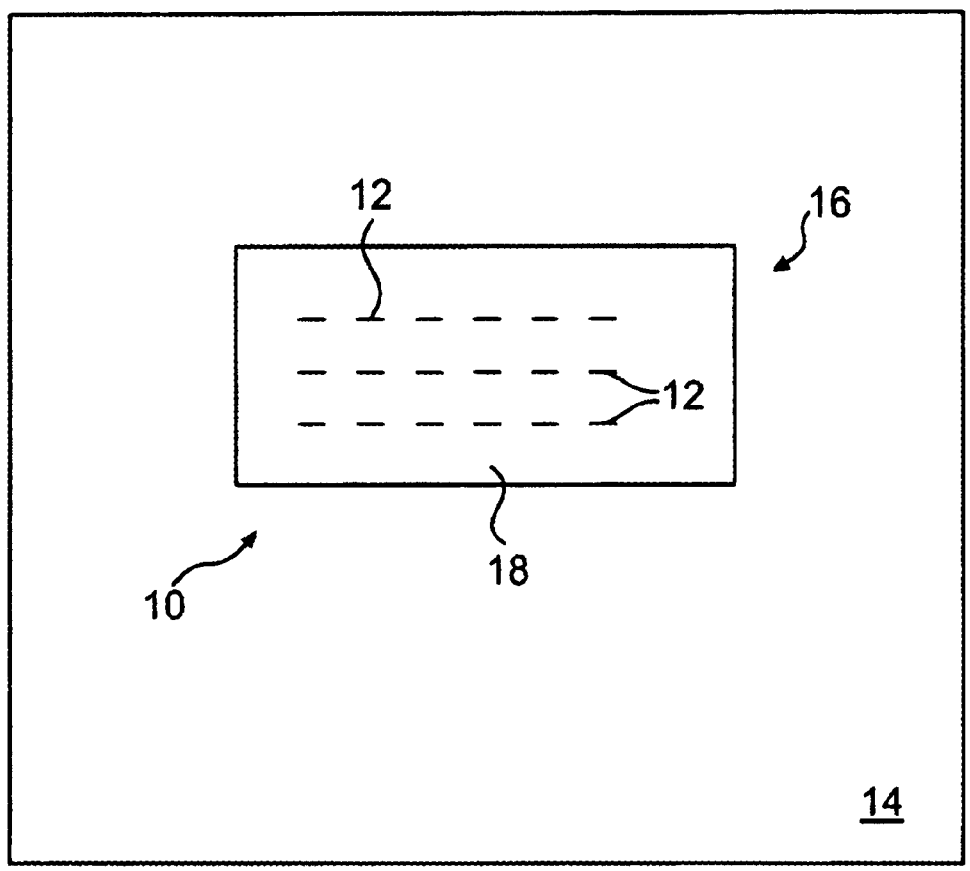

The invention relates to an implant intended to provide mechanical reinforcement, in particular for manual or mechanical tissue sutures.

In surgical operations, in particular in the domain of thoracic surgery, it is usual either to sever and thus remove a part of certain organs, which must then be reclosed with sutures, or to repair existing structures, this being more particularly in the cardiovascular domain.

In either case, manual or mechanical sutures are inserted (by means of a pair of forceps with two branches, one of which is equipped with staples, the other being used as an anvil), intended to limit any leakages, whether they are blood leakages or air leaks, in particular in the context of lung surgery. The difficulty in obtaining a leak proof seal with regard to blood and/or air poses a real problem for a practitioner, since the inserted sutures weakens the tissues, which then have a tendency to tear, as these tissues also already being weakened by the pathology. This fragility leads to air leaks in the context of lungs, and more generally blood leakages, which require drains to be implanted and maintained, leading, in the case of prolonged leakages, to an increase in the length of hospitalization of the patient and, consequently, to a significant increase in the corresponding costs.

In order to overcome these major drawbacks, it has been proposed to implant reinforcement implants which are made of PTFE (polytetrafluoroethylene) and which are in the form of a cylindrical or in form of a parallelepiped sheath or sleeve, intended to move into position by simply sliding over the two branches of a pair of suturing forceps of a type which is known per se. The activating of such a pair of forceps induces the fitting of staples on both sides of the suture line, thus attaching said sleeve to the organ in question. On certain types of forceps, this activation also induces the severing of the organ and of the sleeve, in such a way that only a part of said sleeve remains on the residual organ, acting as a splint-type suture reinforcement.

Flat PTFE splints also exist which, when cut into bands, reinforce manual sutures made using a resorbable or non-resorbable thread.

While, certainly, the implanting of such an implant leads to the mechanical reinforcement of the suture, on the other hand, besides its most particularly high price, such an implant is not bioresorbable. This drawback is particularly troublesome in the event of infection.

The use, in the same way, of cylindrical or flat splints prepared from glutaraldehyde-fixed bovine pericardium has also been proposed. In the same way as in the case above, with such an implant, a high price is encountered. Moreover, and especially, the viral innocuity of these products is uncertain and, in particular, the innocuity with respect to prions is entirely questionable and random.

In other words, the use of such splints may serve as a vector for the transmission of viruses or of prions and therefore, because of this, prove dangerous. Moreover, such splints are also not bioresorbable.

The object of the invention is to provide implants for reinforcing tissue sutures, which have bioresorption, elasticity as well as flexibility properties which make it possible to adjust perfectly to the tissue support and optimize the tightness of the sutures with respect to gas and/or blood, this being at a reasonable cost price.

The object of the invention is also to provide an implant which is totally innocuous, after sterilization, with regard to the transmission of viruses or of prions.

Another object of the invention is to provide a reinforcement implant for tissue sutures which is capable of promoting the cicatrization of the tissues thus protected, with the aim of reducing the length of drainage and of hospitalization, and therefore the costs, and of not constituting an aggravating factor in the event of infection. This resorbable implant makes it possible to obtain a decrease in the inflammatory reaction.

Finally, the invention is also directed toward providing a reinforcement implant for tissue sutures which is capable of presenting a certain leak proof sealingness, in particular with respect to air and to biological fluids (blood, lymph, digestive juices), in the organs thus sutured.

In order to provide further understanding of the present invention, reference is made to the figures and in particular to FIG. 1 which shows implantation of a first embodiment of the present invention in which a woven fabric obtained from polyuronic acid provides a reinforced implant material that is then stapled to human lung tissue to thereby provide a reinforced implant.

This reinforcement implant for tissue sutures, which is intended to be used for mechanically reinforcing sutured tissue zones, is characterized in that it consists of a textile sheet made from polyuronic acid, or from the salts thereof.

This fibrous or filamentous textile sheet can be of the woven, knitted or unwoven type.

While, certainly, the cicatrizing and contact hemostatic properties of polyuronic acid, or of the compounds thereof, are known, on the other hand, its use as a reinforcement implant for sutures, which is as one with the sutures, has never been proposed.

According to the invention, the polyuronic acid $[C_6H_8O_6^-]_n$ is employed directly, in the form of oxidized cellulose obtained from plants (plants, wood), or in the form of calcium alginate, i.e. calcium salts of polyuronic acid $[C_6H_8O_6^-]_n \, Ca^{2+}_m$.

Advantageously, this calcium alginate is obtained from algae.

Textilization of the calcium aginate: a unwoven fibrous sheet is prepared in the following way. A weigh-feeder is fed with calcium alginate fibers of given length, said feeder supplying a card. At the card outlet, a net is obtained which is folded over on itself several times, in order to form a cloth which is bonded together by needle-punching or interlacement, or alternatively by spraying of fluid. In this way, a unwoven felt of relatively high density is obtained, which is able to confer high mechanical resistance on the implant for the purpose of fulfilling its suture reinforcement function. However, this density is not too high, so as to confer elasticity and flexibility on the implant such that perfect adjustment to the tissue support and, as a consequence, the desired optimum tightness with respect to blood and gas are achieved.

The textilization of the cellulose makes use of knitted fabric, which provides neighboring mechanical properties. It then undergoes a chemical oxidation treatment.

This felt or this knitted fabric can be used in flat splints which are cut, on demand, to the desired sizes. In addition, they are flexible to the point that they can be in the form of sheaths or sleeves which are able to move into position by simply sliding over the two branches of a pair of suturing forceps of a type which is known per se, and which is sold, for example, under the trademark SEAMGUARD by W. L Gore & Associates, Inc., or alternatively under the trademark PERIPATCH by Mitroflow International, Inc.

Figure 2:
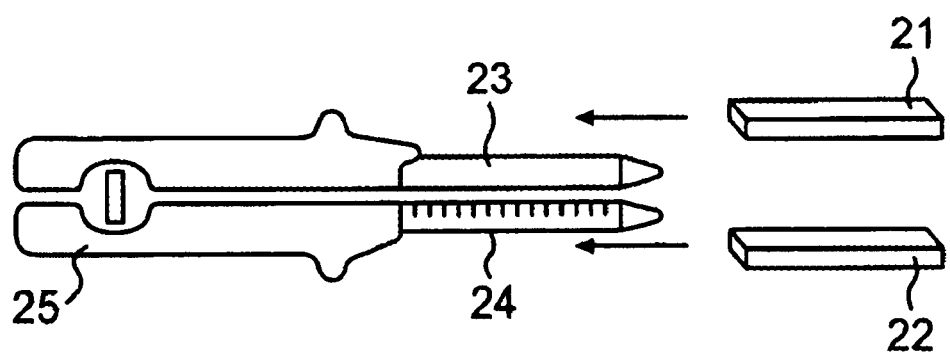
Figure 3:
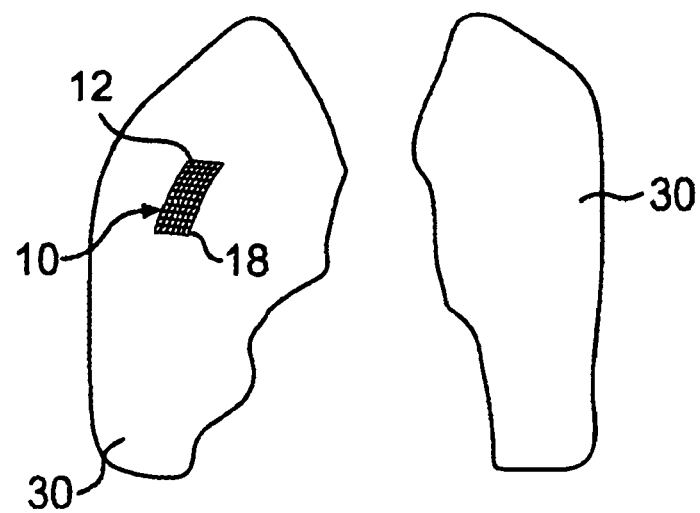

For example, referring to FIG. 2, reinforcement sleeves including cartridge fork sleeve 21 and anvil fork sleeve 22 which are slipped over the anvil fork 23 and cartridge fork 24 of a mechanical stapling device 25, respectively. FIG. 3 provides a more detailed view of the anvil fork sleeve 22 and anvil fork 23 prior to firing of the mechanical stapling device 25. In use, the mechanical stapling device 15 positions four lines of titanium staples on biological tissue with a knife placed between the two middle lines when the stapler 15 is fired. Then, the organ is stapled and divided into two parts. One of the parts stays in the body and the other is trimmed off.

Referring now to FIG. 4, the mechanical stapling device 25 is depicted after firing and the staple line reinforcement material comprising the material of the respective cartridge sleeve 21 and anvil sleeve 22, acts to prevent biological tissue 46 from tears and ruptures around the staples 47 which create a lot of wounds. Thus, cartridge fork sleeve 21, anvil fork sleeve 22 and staple 47 provide reinforcement to the biological tissue 46.

Referring now to FIG. 5, several possible shapes of fork sleeves and anvil sleeves are depicted in FIGS. 5a–5d as sleeves 51–54, respectively. Depending on the suturing forceps used, the desired reinforcement, and target tissue, one of the four sleeves 51–54 may be used.

Advantageously, the implants thus obtained are rendered leak proof by impregnation, and in particular by soaking in an aqueous solution of an ester of polyuronic acid or of the salts thereof, and for example with a solution of 3% sodium alginate ester. This aqueous solution of sodium alginate ester is prepared from Propylene Glycol Alginate, available in the pharmacopeia.

After this impregnation step, said implants are dried in a sterile atmosphere.

In this way, implants for reinforcing sutures are obtained which almost completely abolish air and liquid leakages from said sutures.

Such reinforcement implants for sutures are most particularly indicated for tissue sutures, in particular for lung tissues in the context of lobe exereses, in the context of surgery to reduce pulmonary volume, of surgery for pulmonary emphysema, of pneumothorax, of segmental and atypical resections (WEDGES) and of pulmonary bulla resections. In all these cases, tightness with respect to blood and gas are required.

The problems engendered by this tightness deficiency, in particular by the need to maintain the drainage, prolonging, as already mentioned, the patient's stay in hospital and in fact putting a significant strain on the cost resulting therefrom, but also on the morbidity, are in fact known.

However, such implants are also most particularly suitable in the context of bronchial, digestive, cardiovascular or urogenital suture reinforcements, which are only required to be bloodtight (bronchial sutures also needing to be gastight).

In the various contexts of implantation of the implant in accordance with the invention, it can be used:

either as a reinforcement implant for a mechanical suture using a pair of suturing forceps of the type mentioned above, and therefore be in the form of a cylindrical or in form of a parallelpided sheath which fits over the two branches of the forceps, or more conventionally as a reinforcement implant for a manual suture made using threads and needles, and, in this case, it is in the form of bands or strips which are approximately rectangular in shape and are cut, on demand, from a sheet which is bigger in size.

The use of such a material based on polyuronic acid, or on the salts thereof, promotes airostasis, hemostasis and cicatrization, resulting in faster healing of the patients.

Its woven, knitted or unwoven structure also allows a conformation at manufacturing which is suitable for each of the mechanical stapler models available on the market, including for those used in video surgery or surgery under celioscopy. Depending on the type of forceps and the type of stapler, one or two sleeves are required (anvil and staple-loader, or anvil or loader isolated).

Moreover, the material used is both biocompatible and resorbable within a typical time period of three months.

In addition, given the plant origin of the material used, total innocuity of the implant, both with respect to viruses and with respect to prions, is obtained, conferring upon it, in fact, high safety of use.

Finally, by virtue of the nature of the compounds used, the cost for producing such implants proves to be entirely moderate and thus capable of promoting their development and the extension of the indications for implantation.

What is claimed is:

1. A reinforcement implant for air and fluid leak proof surgical sutures, to be used inside human and animal bodies, said implant comprising:
   a strip made of fibrous or filamentous textile material made with polyuronic acid, or the salts thereof, and
   an impregnating element of said textile material comprising an ester of polyuronic acid in aqueous solution.

2. The reinforcement implant according to claim 1, wherein the strip is made of woven material.

3. The reinforcement implant according to claim 1, wherein the strip is made of knitted material.

4. The reinforcement implant according to claim 1, wherein the polyuronic acid is oxidized cellulose.

5. The reinforcement implant according to claim 1, wherein the polyuronic acid is calcium alginate.

6. The reinforcement implant according to claim 5, wherein said calcium alginate is a salt extracted from an algae.

7. The reinforcement implant according to claim 1, wherein the ester of polyuronic acid is a sodium alginate ester.

8. A reinforcement implant for air and fluid leak proof surgical sutures, to be used inside human and animal bodies, said implant comprising:
   a sleeve made of fibrous or filamentous textile material made with polyuronic acid, or from the salts thereof, and
   an impregnating element of said textile material comprising an ester of polyuronic acid in aqueous solution wherein said implant is biologically resorbable.

9. The reinforcement implant according to claim 8, wherein the sleeve is made of woven material.

10. The reinforcement implant according to claim 8, wherein the filamentous textile material is a knitted material.

11. The reinforcement implant according to claim 8, wherein the sleeve is in the form of a parallelipiped.

12. A method of manufacturing a reinforcement implant, for air and fluid leak proof surgical sutures, comprising the steps of:
   after textilizing calcium alginate for obtaining a knitted or woven fabric of filamentous material of said alginate,
   cutting said knitted or woven fabric into implants of predetermined shapes and dimensions,
   impregnating said implants by soaking said implants within an aqueous solution of an ester of polyuronic acid or of the salts thereof, and
   drying said implants in a sterile atmosphere.

13. The method according to claim 12, wherein said impregnation is provided in an aqueous solution of sodium alginate ester.

14. A method of placing a leak proof reinforcement implant within a human or an animal body, said implant having a sleeve shape and being made of sleeve of knitted or woven fabric of filamentous material made with polyuronic acid impregnated with an ester of polyuronic acid in aqueous solution, said method comprising the steps of:
  pinching said sleeve with a pair of suturing forceps, said pair of suturing forceps having two branches,
  placing said sleeve upon the part of the human or animal body to be reinforced and stapling said implant on said part of the human body.

15. A reinforcement implant for air and fluid leak proof surgical sutures, to be used inside human and animal bodies, said implant consisting of:
  a strip, sheath or sleeve made of fibrous or filamentous textile material based on polyuronic acid or the salts thereof, and
  said strip, sheath or sleeve being impregnated with an aqueous solution of an ester of polyuronic acid.

16. A reinforcement implant for air and fluid leak proof surgical sutures to be used inside human and animal bodies, said implant comprising:
  a strip, sheath or sleeve made of fibrous or filamentous textile material made from polyuronic acid, or from the salts thereof, and
  an impregnating element of said textile material comprising an ester of polyuronic acid in aqueous solution.

* * * * *